United States Patent [19]
Gould et al.

[11] 3,956,470
[45] May 11, 1976

[54] PENTAFLUOROSULFUR HYPOCHLORITE

[75] Inventors: Douglas Eugene Gould, Boonton; David Edward Young, Denville; Lowell Ray Anderson, Parsippany; William Burke Fox, Morristown, all of N.J.

[73] Assignee: Allied Chemical Corporation, New York, N.Y.

[22] Filed: June 6, 1968

[21] Appl. No.: 734,891

[52] U.S. Cl............................ 423/466; 252/186; 252/426; 252/439; 260/465.7; 260/694; 423/467; 424/162; 424/167
[51] Int. Cl.² .......................................... C01B 7/24
[58] Field of Search ............. 23/367, 203; 252/441; 423/466, 467

[56] References Cited
UNITED STATES PATENTS

| | | | |
|---|---|---|---|
| 3,035,893 | 5/1962 | Roberts.................... | 23/367 |
| 3,359,081 | 12/1967 | Tullock et al............. | 23/367 |
| 3,582,292 | 6/1971 | Schack et al............. | 23/367 |
| 3,627,799 | 12/1971 | Young et al.............. | 260/543 R X |

OTHER PUBLICATIONS

Lustig et al., "Journal of the American Chemical Society," Vol. 89, pp. 2841–2843 (June 7, 1967).
Mellor, "Comprehensive Treatise on Inorganic and Theoretical Chemistry," Supplement II, Part I, p. 150 (1956).
Ruff et al., "Inorganic Chemistry," Vol. 3, pp. 1422–1425 (1964).
Dudley et al., "Pentafluorosulfur Hypofluorite and Thionyl Tetrafluoride," J. Am. Chem. Soc. 78 (1956), pp. 1553–1557.
Hohorst et al., "Bis(fluoroxy) difluoromethane, $CF_2(OF)_2$," J. Am. Chem. Soc. 89 (1967), pp. 1809–1810.

*Primary Examiner*—Herbert T. Carter
*Attorney, Agent, or Firm*—Robert A. Harman; Arthur J. Plantamura

[57] ABSTRACT

Pentafluorosulfur hypochlorite, $SF_5OCl$, and its preparation by reacting thionyl tetrafluoride, $SOF_4$, or a salt thereof, with an inorganic reagent containing a chlorine atom in a +1 oxidation state which chlorine atom is attached to a more electronegative element. When $SOF_4$ is employed, it is necessary to use a catalyst for the reaction selected from the group consisting of LiF, NaF, KF, RbF and CsF. Pentafluorosulfur hypochlorite is useful as a polymerization initiator and is a valuable intermediate for the synthesis of other useful compounds.

17 Claims, No Drawings

PENTAFLUOROSULFUR HYPOCHLORITE

BACKGROUND OF THE INVENTION

Pentafluorosulfur hypofluoride, $SF_5OF$, is disclosed by Williamson et al., Inorganic Chemistry, Vol. 1, pp. 673–677 (1962). Williamson et al. disclose that $SF_5OF$ does not react with CO at room temperature but that these materials do react when temperature is raised to 165°C. The disclosed products of this reaction are carbonyl fluoride, $F_2CO$, and thionyl tetrafluoride, $SOF_4$.

SUMMARY OF THE INVENTION

We have discovered the compound pentafluorosulfur hypochlorite, $SF_5OCl$. This compound possesses unusual properties not possessed by the closely related prior art compound $SF_5OF$. $SF_5OCl$ is useful as a source of active chlorine which can be taken advantage of in bleaches and as a chlorinating agent, capable of chlorinating unsaturated bonds in organic compounds and to replace hydrogen atoms in organic molecules. Fumes of the subject hypochlorite are toxic to insects and other animal life.

One unexpected property possessed by $SF_5OCl$ is that, unlike $SF_5OF$, $SF_5OCl$ reacts readily with carbon monoxide even at room temperature and below, to yield pentafluorosulfur chloroformate, $SF_5OC(O)Cl$. $SF_5OC(O)Cl$ is useful as a catalyst for the polymerization of unsaturated compounds and in the preparation of polycarbonates, polyesters and formaldehyde polymers.

Another unexpected property is that at room temperature, $SF_5OCl$ reacts with ECN, wherein E is an electronegative group, to form $CF_2ENCl_2$. For example, $SF_5OCl$ reacts with ClCN, cyanogen chloride, to form $CF_2ClNCl_2$. This compound is useful as an initiator for the polymerization of fluoroolefins and as a fumigant and rodent killer. When it is attempted to react the corresponding $SF_5OF$ compound under similar conditions, no reaction takes place.

Another aspect of the invention is that the novel $SF_5OCl$ compound may be prepared by reacting a starting material consisting of thionyl tetrafluoride, $SOF_4$, or a salt thereof, with an inorganic chlorinating reagent containing a chlorine atom in a +1 oxidation state, which chlorine atom is attached to a more electronegative element. Where $SOF_4$ is used as the starting material, it is necessary to use a catalyst for the reaction selected from the group consisting of LiF, NaF, KF, RbF and CsF. Where the salts are used as starting materials, the reaction will proceed satisfactorily without a catalyst but higher yields may be obtained by using the same type of catalyst described above.

DETAILED DESCRIPTION AND PREFERRED EMBODIMENTS

The starting material may be $SOF_4$ or a salt thereof having the formula $SF_5OM$, wherein M is a metal selected from the group consisting of Li, Na, K, Rb and Cs. These salts may readily be prepared by heating $SOF_4$ with a metal fluoride of the formula MF wherein M is as defined above. Low yields of these salts are obtained even at very low temperatures, however, it has been found that excellent yields of the salt are obtained when the reactants are heated in a closed reactor to 100°C. and the reaction is allowed to proceed under the autogeneous pressure developed in the reactor at that temperature. Preferably, the reactor is agitated or shaken during the reaction and a large excess of $SOF_4$, say in the order of 2–5 fold is employed. The salts are solids and are best recovered by providing a large enough excess of $SOF_4$ to ensure complete reaction and pumping off the unreacted $SOF_4$. Reaction mixtures in which incomplete conversion to the salts is effected, in other words wherein residual quantities of the MF are present, may still readily be used as starting material for the main reaction. The excess of MF material present will then serve as catalyst for the reaction.

The chlorinating reagent which is reacted with the starting compound is an inorganic reagent which contains a chlorine atom in a +1 oxidation state, which chlorine atom is attached to a more electronegative element. Illustrative suitable chlorinating agents are ClF, $Cl_2O$, $ClONO_2$, NaOCl and $ClOSO_2F$. The preferred reagents are ClF and $Cl_2O$. Other suitable inorganic chlorinating agents within the scope of the invention will readily occur to one skilled in the art.

Reaction temperatures for the main reaction vary over a very wide range. Generally, the reaction proceeds readily even at low temperatures. For example, reaction with ClF will take place readily at about −78°C. The reaction will proceed easily at temperatures up to 25°C. and higher but in view of the ready reaction at lower temperatures there is no advantage in supplying heat to the reaction. Preferred temperatures range from −78°C. to 0°C. and most preferably are in the order of about −20°C. Depending upon the particular starting material and inorganic chlorinating reagent employed, the optimum reaction temperature may vary within the above indicated range. The optimum temperature range for a particular reaction can be determined in a routine fashion.

Atmospheric, sub- or super-atmospheric pressures may be employed in the practice of the invention process.

The chlorination reactions described herein can be carried out with the reactants in vapor, liquid phase or solid phase. In the latter case any inert solvent is preferably employed, if desired. Halogenated hydrocarbons, such as $CFCl_3$, for example, are useful for this purpose. The catalysts are used in solid phase.

The stoichiometry of the reaction requires one mol of inorganic chlorinating reagent per mol of starting compound. In order to ensure complete reaction, at least the stoichiometric amount or a slight excess of reagent should be employed. There is no advantage in employing large stoichiometric excesses of the chlorinating reagents although large excesses of the same will not deleteriously affect the reaction.

The catalysts employed, which are mandatory for the $SOF_4$ reaction and optional for the $SF_5OM$ reaction, may be selected from the group consisting of LiF, NaF, KF, RbF and CsF. The preferred catalysts are CsF, RbF and KF, particularly CsF. The amount of catalyst employed is not critical. Very small amounts will serve to catalyze the reaction and very large amounts will not deleteriously affect the reaction. Generally, about 0.1–3 mols catalyst/mol of the starting compound is employed with the preferred ratio being between about 0.5–1 mols catalyst/mol of starting compound.

The materials of construction for the apparatus used should be inert to the reactants employed. Stainless steel and fluoropolymers, e.g., polytetrafluoroethylene and polychlorotrifluoroethylene are illustrations of suitable types of materials for this purpose.

In the following examples, parts and percentages are by weight unless otherwise indicated.

EXAMPLE 1

A 30 ml stainless steel "Hoke" cylinder is charged with an unweighed amount of dry, finely ground CsF. The cylinder is then fitted with a stainless steel "Hoke" needle valve. Conventional vacuum techniques, using a metal-(nickel-"Monel")"Plaskon"(TM of Allied Chemical Corporation for a polymer of chlorotrifluoroethylene) type fluoropolymer system, are used to condense 10 mmol of $SOF_4$ and 10 mmol of ClF into the cylinder at about −196°C. The mixture is allowed to warm to −20°C. and is stored overnight at that temperature. At the end of this period the infrared spectrum of the gaseous product shows practically no absorption associated with the S=O stretch in $SOF_4$ (1390 cm$^{-1}$). New strong bands are present at 926 cm$^{-1}$ and 890 cm$^{-1}$ in the S-F stretching region. Fractionation of this material through a −111°C. cold trap gives a product identified as $SF_5OCl$.

Analysis: Calculated for $SF_5OCl$: %S, 17.96; %F, 53.22; %Cl, 19.86 Found: %S, 17.11; %F, 51.30; %Cl, 19.09

EXAMPLE 2

10 mmol of $SOF_4$ is added to an unknown but deficient amount of CsF and the mixture is heated in a closed reactor at about 100°C. for about 24 hours. The mixture is then allowed to cool and there is obtained the following salt $SF_5O^-Cs^+$. A slight excess of $Cl_2O$ is added to this salt and the mixture is cooled to −20°C. and maintained at that temperature for a period of 20 hours. At the end of this period the resulting mixture is fractionated through a −123°C. cold trap and gives a product having the same infrared spectrum as the product of Example 1 and is identified as $SF_5OCl$.

EXAMPLE 3

Conventional vacuum techniques as described in Example 1, are used to combine $SF_5OCl$ with a slight excess of CO in a 30 ml. stainless steel "Hoke" cylinder fitted with a stainless steel "Hoke" needle valve. After overnight storage at −20°C., the cylinder is cooled to −196°C. and the excess CO pumped off. Fractionation through a −95°C. trap results in the collection of $SF_5OC(O)Cl$ in the trap. Identity of the product is confirmed by elemental, infrared and nuclear magnetic resonance spectrum analyses, as well as by a molecular weight determination.

Analysis: Calculated for $SF_5OC(O)Cl$: %Cl, 17.20; %F, 46.00; %C, 5.81; %S, 15.53 Found: %Cl, 17.80; %F, 45.32; %C, 5.71; %S, 15.36

EXAMPLE 4

A. Reaction of $SF_5OCl$ with ClCN. About 10 mmol of $SF_5OCl$ and about 10 mmol of ClCN are condensed together into a 225 cc stainless steel reactor equipped with a "Hoke" needle valve. The mixture is then allowed to warm to room temperature and permitted to stand for several days. A reaction takes place and the products are identified by elemental analysis, molecular weight determination, infrared and nuclear magnetic resonance analyses as being $CF_2ClNCl_2$ and $SOF_4$.

B. It is attempted to react $SF_5OF$ and ClCN under the same conditions described in part A. After the same reaction period, no change in the starting material is observed and there is no evidence supporting the formation of the corresponding difluoro-substituted $CF_2ClNF_2$ product.

We claim:
1. $SF_5OCl$.
2. The process for preparing the compound of claim 1 which comprises reacting $SOF_4$ with an inorganic chlorinating reagent containing a chlorine atom in a +1 oxidation state, which chlorine atom is attached to a more electronegative element, in the presence of an alkali metal fluoride selected from the group consisting of LiF, NaF, KF, RbF and CsF at about −78° to +25°C.
3. The process according to claim 2 in which the inorganic chlorinating reagent is ClF or $Cl_2O$.
4. The process according to claim 3 in which the alkali metal fluoride is selected from the group consisting of KF, RbF and CsF.
5. The process according to claim 4 wherein the inorganic chlorinating reagent is ClF.
6. The process according to claim 4 wherein the inorganic chlorinating reagent is $Cl_2O$.
7. The process according to claim 5 wherein the alkali metal fluoride is CsF.
8. The process according to claim 6 wherein the alkali metal fluoride is CsF.
9. The process for preparing the compound of claim 1 which comprises reacting a starting compound of the formula $SF_5OM$, wherein M is selected from the group consisting of Li, Na, K, Rb and Cs, with an inorganic chlorinating reagent containing a chlorine atom in a plus one oxidation state, which chlorine atom is attached to a more electronegative element at about −78° to +25°C.
10. The process according to claim 9 in which the inorganic chlorinating reagent is ClF or $Cl_2O$.
11. The process according to claim 10 in which the inorganic chlorinating reagent is ClF.
12. The process according to claim 11 in which M is Cs.
13. The process according to claim 10 in which the inorganic chlorinating reagent is $Cl_2O$.
14. The process according to claim 13 in which M is Cs.
15. The process according to claim 2 wherein the reaction temperature is about −20°C.
16. The process according to claim 9 wherein the reaction temperature is about −20°C.
17. A process for preparing chloroxysulfurpentafluoride of the formula $SF_5OCl$ comprising reacting chlorine monofluoride and thionyl tetrafluoride at a temperature from 0°C. to −78°C. in the presence of a member selected from the group consisting of potassium fluoride, rubidium fluoride and cesium fluoride to produce said chloroxysulfurpentafluoride.

* * * * *